(12) United States Patent
Boston et al.

(10) Patent No.: US 6,599,722 B2
(45) Date of Patent: *Jul. 29, 2003

(54) METHOD FOR PRODUCING ASCORBIC ACID INTERMEDIATES

(75) Inventors: Matthew Grant Boston, San Carlos, CA (US); Barbara A. Swanson, San Francisco, CA (US)

(73) Assignee: Genencor International, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/218,700

(22) Filed: Dec. 22, 1998

(65) Prior Publication Data

US 2002/0177197 A1 Nov. 28, 2002

(51) Int. Cl.$^7$ ............... C12P 7/58; C12P 7/26; C12P 1/04; C12N 9/04
(52) U.S. Cl. ............ 435/137; 435/41; 435/132; 435/148; 435/170; 435/190
(58) Field of Search ............... 435/132, 148, 435/137, 41, 170, 190

(56) References Cited

U.S. PATENT DOCUMENTS

| | | | |
|---|---|---|---|
| 3,790,444 A | 2/1974 | Shunichiroi et al. | 435/137 |
| 4,757,012 A | 7/1988 | Estell et al. | 435/479 |
| 4,758,514 A * | 7/1988 | Light et al. | 435/91 |
| 4,945,052 A | 7/1990 | Hardy et al. | 435/126 |
| 5,004,690 A | 4/1991 | Light et al. | 435/138 |
| 5,008,193 A | 4/1991 | Anderson et al. | 435/138 |
| 5,032,514 A | 7/1991 | Anderson et al. | 435/138 |
| 5,240,843 A | 8/1993 | Gibson et al. | 435/188 |
| 5,376,544 A | 12/1994 | Lazarus et al. | 435/190 |
| 5,583,025 A | 12/1996 | Lazarus et al. | 435/190 |
| 5,795,761 A * | 8/1998 | Powers et al. | 435/190 |

FOREIGN PATENT DOCUMENTS

| | | |
|---|---|---|
| EP | 0046284 A | 2/1982 |
| EP | 0088409 A | 9/1983 |
| EP | 0292303 A | 11/1988 |
| EP | 0 132 557 | 10/1990 |
| WO | WO 94/05772 A | 3/1994 |

OTHER PUBLICATIONS

Aiguo et al., "Synthesis of a 2–keto–L–gulonic Acid from Gluconic Acid by Co–Immobilized *Gluconobacter Oxydans* and *Corybacterium sp.*," *Biotechnology Letters*, vol. 20, No. 10, pp. 939–942 (1998).

Bovara et al., "A New Enzymatic Route to the Synthesis of 12–Ketoursodeoxycholic Acid," *Biotechnology Letters*, vol. 18, No. 3, pp. 305–308 (1996).

Bowen et al., "Redox Enzymes in Industrial Fine Chemical Synthesis," *Chemistry and Industry*, pp. 323–326, May 20, 1985.

Bui Nguyen, "Application of high–performance liquid chromatography to the separation of ascorbic acid from isoascorbic acid," *J. Chrom.*, 196:163–165 1980.

Bunton et al., "The Determination of Ascorbic and Erythorbic Acids in Meat Products," *J. Assoc. Pub. Analysts*, 17:105–110 1979.

Candau et al., "In vivo channeling of substrates in an enzyme aggregate for β–carotene biosynthesis," *Proc. Natl. Acad. Sci. USA*, V. 88 pp. 4936–4940, Jun. 1991 Biochemistry.

Frey et al., The Molecular biology of IncQ plasmids. In: Thomas (Ed.), *Promiscuous Plasmids of Gram Negative Bacteria*, Academic Press, London, pp. 79–94, 1989.

Frey et al., "Replication and copy number control of the broad–host–range plasmid RSF1010", *Gene*, 113 (1992) 101–106.

Grindley et al., "Conversion of Glucose to 2–Keto–L–Gulonate, an Intermediate in L–Ascorbate Synthesis, by a Recombinant Strain of *Erwina citreus*," *Applied and Environmental Microbiology* 54(7): 1770–1775) 1988.

Hummel, Werner, "Enzyme–Catalyzed Synthesis of Optically Pure $ (+)–Phenylethanol," *Biotechnology Letters*, V. 12 (6) pp. 403–408 (1990).

Ikemi et al., "The Membrane Bioreactor with Coenzyme Recycling System," *Journal of Biotechnology* 14, pp. 211–220 (1990).

Izumi et al., "NADH Production from NAD+ using a Formate Dehydrogenase System with Cells of a Methanol–Utilizing Bacterium," *J. Ferment. Technol.* 61:2 (1983) pp. 135–142.

Kise et al., "Two–Phase System Membrane Reactor with Cofactor Recycling," *Journal of Biotechnology* 14, pp. 221–228 (1990).

Kragl et al., "Continuous Production of L–tert–leucine in Series of Two Enzyme Membrane Reactors," *Bioprocessing Engineering* 14, pp. 291–297 (1996).

Kulbe et al., "Enzyme–Catalyzed Production of Mannitol and Gluconic Acid", *Annals of the New York Academy of Sciences*, vol. 506, 1987, pp 552–568.

Matsuno et al., "Large–Scale Production of Chiral Alcohols with High Enantiomeric Excess Through Yeast–Mediated Asymmetric Reduction of Prochiral Ketones," *Enzyme Engineering XII*, Eds. Legoy et al. New York: New York Academy of Sciences, pp. 473–4761995.

(List continued on next page.)

Primary Examiner—Elizabeth Slobodyansky
(74) *Attorney, Agent, or Firm*—Richard T. Ito (57) ABSTRACT

The present invention relates to non-fermentative methods for the production of ASA intermediates, KDG, DKG and KLG and methods for the regeneration of co-factor. The invention provides genetically engineered host cells comprising heterologous nucleic acid encoding enzymes useful in the process.

24 Claims, 5 Drawing Sheets

OTHER PUBLICATIONS

McIntire et al. "Identification of the covalently bound flavins of D–bluconate dehydrogenases from *Pseudomonas aeruginosa* and Pseudomonas fluorescens and of 2–keto–D–gluconate dehydrogenase from *Gluconobacter melanogenus*", *Biochem. J.* (1985) 231, 651–654).

Matsushita et al., "Membrane–Bound D–Gluconate Dehydrogenase from *Pseudomonas aeruginosa*," 1979, *J. Biochem.* 85:1173–1181.

Neijssel et al., "Physiological Significance and Bioenergetic Aspects of Glucose Dehydrogenase", *Antonie Van Leeuwenhoek*, vol. 56, 51–61, 1989.

Nidetzky et al., "Carry Out Coenzyme Conversions Economically," *Chemtech*, pp. 31–36 (Jan. 1996).

Nidetzky et al., "Improved Operational Stability of Cell–Free Glucose–Fructose Oxidoreductase form *Zymonas mobilis* for the Efficient Synthesis of Sorbitol and Gluconic Acid in a Continuous Ultrafiltration Membrane Reactor," 1997 John Wiley & Sons, pp. 624–629.

Obon et al, "Continuous Retention of Native NADP(H) in an Enzyme Membrane Reactor for Gluconate and Glutamate Production," *Journal of Biotechnology* 50, pp. 27–36 (1996).

Pachla et al., "Determination of Ascorbic Acid in Foodstuffs, Pharmaceuticals, and Body Fluids by Liquid Chromatography with Electrochemical Detection", *Analytical Chemistry*, vol. 48, No. 2, Feb. 1976, pp 364–367.

Pugh, "Immobilized Redox Enzymes and Their Use as Catalysts for Fine Chemical Synthesis," *Enzymes as Catalysts in Organic Synthesis*, Ed. Schneider, M.P. Dondrecht, Germany: D. Reidel Publishing Company, pp. 217–232.

Reichstein and Grussner, Eine ergiebige Synthese der I–Ascorbisaure (C–Vitamin)2) Helv. Chem. Acta., 17, 311–328 (1934).

Riva et al., "Oxidoreduction of Steroids with Immobilized Hydroxysteroid Dehydrogenases and Cofactor Regeneration," *Annals of the New York Academy of Sciences*, V. 542 (1988).

Schmidt et al., "Multiple Steady States in a Coupled Enzyme System Represented by the Enzymatically Catalyzed Production of L–Phenylalanine," *Annals of the New York Academy of Sciences*, V. 501 1987.

Schneider et al., "Utilizaiton by yeasts of D–glucarate, galactarate, and L–tartarate is uncommon and occurs in strains of Cryptococcus and Trichosporan," *Journal canadien de Microbiologie*, V. 36, N. 12 Dec. 1990.

Seelbach et al., "Nanofiltration membranes for cofactor retention in continous enzymatic synthesis," *Enzyme and Microbial Technology*, 20:389–392, 1997.

Shinagawa et al., "2–Keto–D–gluconate Dehydrogenase from Gluconobacter melanogenus, Membrane–Bound, *Oxidation–Reduction Enzymes*", Methods in Enzymology, vol. 89, pp 194–198, 1991.

Simons et al., "Aerobic 2–ketogluconate metabolism of *Klebsiella pneumoniae* NCTC 418 grown in chemostat culture", *Journal of General Microbiology* (1991), 137, 1479–1483.

Smith et al., Purification and characterization of glucose dehydrogenase from the thermoacidophilic archaebacterium Thermophlasma acidophilum, *Biochem. J.* (1989), V.261, 973–977.

Stoshane et al., "Fermentation of Glucose by Acetobacter melanogenus", *Biotechnology and Bioengineering*, vol. XIX, pp. 459–465, 1977.

Woodward et al., "In Vitro Hydrogen Production by Glucose Dehydrogenase and Hydrogenase," *Nature Biotechnology*, vol. 14, pp. 872–874 (Jul. 1996).

* cited by examiner

METHOD FOR PRODUCING ASCORBIC ACID INTERMEDIATES

FEDERALLY SPONSORED RESEARCH OR DEVELOPMENT

This invention was made with Government support under Grant No. 70NANB5H1138 awarded by Advanced Technology Program/National Institute of Standards and Technology. The Government has certain rights in this invention.

FIELD OF THE INVENTION

The present invention relates to pathway engineering and in particular to biocatalytic methods for the production of ascorbic acid intermediates. In particular, the invention provides methods for the production of ascorbic acid intermediates in non-fermentative systems.

BACKGROUND OF THE INVENTION

L-Ascorbic acid (vitamin C, ASA) finds use in the pharmaceutical and food industry as a vitamin and antioxidant. The synthesis of ASA has received considerable attention over many years due to its relatively large market volume and high value as a specialty chemical. The Reichstein-Grussner method, a chemical route from glucose to ASA, was first disclosed in 1934 (Helv. Chim. Acta 17:311–328). Lazarus et al. (1989, "Vitamin C: Bioconversion via a Recombinant DNA Approach", *Genetics and Molecular Biology of Industrial Microorganisms*, American Society for Microbiology, Washington D.C. Edited by C. L. Hershberger) disclosed a bioconversion method for production of an intermediate of ASA, 2-keto-L-gulonic acid (2-KLG, KLG) which can be chemically converted to ASA. This bioconversion of carbon source to KLG involves a variety of intermediates, the enzymatic process being associated with co-factor dependent reductase activity. Enzymatic co-factor regeneration involves the use of enzymes to regenerate co-factors such as NAD+ to NADH or NADP+ to NADPH at the expense of another substrate that is then oxidized.

There remains a need for economically feasible methods for the production of ASA intermediates. In particular, when such methods involve the use of enzymatic activities which require co-factor, it would be particularly desirable to have methods which provide for co-factor regeneration. The present invention addresses that need.

SUMMARY OF THE INVENTION

The present invention relates to the non-fermentative production of ASA intermediates, e.g., KDG, DKG and KLG, and ultimately their conversion to end products, e.g., erythorbate and ascorbic acid, from a carbon source in a biocatalytic environment. See FIG. 2 for a schematic representation of the production of these intermediates and products.

The present invention also relates to a non-fermentative process for the production of ASA intermediates wherein required co-factor is regenerated. The biocatalytic environment may comprise viable or non-viable host cells which contain at least one enzymatic activity capable of processing the carbon source to the desired intermediate.

When KDG is the desired ASA intermediate, the bioreactor is provided with a carbon source which is biocatalytically converted through at least one oxidative step to KDG. In this embodiment, the host cell may comprise a mutation(s) in a gene encoding an oxidative enzymatic activity specific to oxidizing the KDG. When DKG is the desired ASA intermediate, the bioreactor is provided with a carbon source which is biocatalytically converted through at least one oxidative step to DKG. Depending upon the host cell used, the host cell may comprise a mutation(s) in a gene encoding an oxidizing or reducing enzymatic activity such that DKG is not further converted to other intermediates. When KLG is the desired ASA intermediate, the bioreactor is provided with a carbon source which is biocatalytically converted through at least one oxidative step and at least one reducing step to KLG. Depending upon the host cell used, the host cell may comprise a mutation(s) in a gene encoding an oxidizing or reducing enzymatic activity such that KLG is not further converted to other intermediates. When the oxidative step and reducing step require co-factor, the method provides a means for co-factor regeneration. Therefore, the present invention is based, in part, upon the discovery that catalytic amounts of co-factor can be regenerated in a non-fermentative, or in vitro, method for the production of KLG from a carbon source.

The host cells may be recombinant comprising at least one heterologous enzymatic activity. The process may be performed as a batch process or a continuous process. The host cells are preferably members of the family Enterobacteriacea and in one embodiment, the member is a Pantoea species and in particular, *Pantoea citrea*. *Pantoea citrea* can be obtained from ATCC having ATCC accession number 39140, for example.

The host cells may be lyophilized, permeabilized, or otherwise treated to reduce viability or mutated to eliminate glucose utilization for cell growth or metabolism as long as the enzymatic activity is available to convert the carbon source to the desired intermediate. The intermediates may be further processed to the end products of erythorbate or ASA.

Accordingly, in one aspect, the present invention provides a method for the production of the intermediate DKG or KDG from a carbon source comprising enzymatically oxidizing the carbon source by at least one oxidative enzymatic activity to yield DKG or KDG. In another embodiment, the process comprises oxidizing the carbon source by a first oxidative enzymatic activity to yield a first oxidative product and oxidizing said first oxidative product by a second oxidative enzymatic activity to yield KDG. In one embodiment, the first oxidative enzymatic activity is a GDH activity and the second oxidative enzymatic activity is a GADH activity. KDG may be further converted to erythorbate. The process may further comprise oxidizing KDG by a third oxidative enzymatic activity to yield DKG.

For production of KLG, if the carbon source is KDG, the method comprises the steps of enzymatically oxidizing the KDG by at least one oxidative enzymatic activity to an oxidation product; and enzymatically reducing said oxidation product by at least one reducing enzymatic activity to 2-KLG. Alternatively, if DKG is the carbon source, DKG is converted to KLG by a reducing enzymatic activity.

In one embodiment, at least one oxidative enzymatic activity is bound to host cell membranes and in another embodiment, at least one oxidative enzymatic activity is in solution and in another embodiment, at least one enzymatic activity is immobilized. In the process for producing KDG, it is preferred that the host cell comprises a mutation in the nucleic acid encoding a KDGDH activity, such that the KDG is not further oxidized.

The present invention also provides a process for the non-fermentative production of 2-KLG from a carbon source, wherein said process comprises the following steps in any order, enzymatically oxidizing the carbon source by at least one oxidative enzymatic activity to an oxidation product; and enzymatically reducing said oxidation product by at least one reducing enzymatic activity to 2-KLG. In one embodiment, the carbon source is KDG. In another embodiment, said oxidative enzymatic activity requires an oxidized form of an enzymatic co-factor and said reducing enzymatic activity requires a reduced form of said enzymatic co-factor and said oxidized form of said co-factor and said reduced form of said co-factor are recycled between at least one oxidizing step and at least one reducing step.

In another embodiment, the process comprises the following steps in any order: enzymatically oxidizing the carbon source by a first oxidative enzymatic activity to a first oxidation product; enzymatically oxidizing the first oxidation product by a second oxidative enzymatic activity to a second oxidation product; enzymatically oxidizing the second oxidation product by a third oxidative enzymatic activity to a third oxidation product; and enzymatically reducing the third oxidation product by a reducing enzymatic activity to 2-KLG. In one embodiment, at least one of said first, second and third oxidative enzymatic activities requires an oxidized form of an enzymatic co-factor and said reducing enzymatic activity requires a reduced form of said enzymatic co-factor and wherein said oxidized form of said co-factor and said reduced form of said co-factor are recycled between at least one oxidizing step and the reducing step. In one embodiment of the process, the first oxidative enzymatic activity requires an oxidized form of said enzymatic co-factor.

In one embodiment of the process, the carbon source is glucose and said first oxidative enzymatic activity is a glucose dehydrogenase activity. The glucose dehydrogenase activity may be obtained from a bacterial, yeast or fungal source, including *T. acidophilum, Cryptococcus uniguttalatus* and Bacillus species. In another embodiment, each of said first, said second enzyme and said third enzymatic activities is a dehydrogenase activity. In one embodiment, at least one of said first, said second, said third and said fourth enzyme activities are immobilized, in another at least one is in solution and in another at least one is bound to the membrane of a viable or non-viable host cell.

In a further embodiment, the second oxidative enzymatic activity is a GADH and the third oxidative enzymatic activity is KDGDH. In another embodiment, the reductase activity is obtainable from a bacterial, yeast or fungal source and in a preferred embodiment is 2,5 DKG reductase.

In yet another embodiment of the method, the first oxidation product is gluconate, the second oxidation product is 2-KDG, and the third oxidation product is 2,5-DKG.

In a further embodiment of the process, the recombinant host cell has a mutation of at least one naturally occurring dehydrogenase activity and is preferably a deletion in the naturally occurring membrane bound GDH activity. The host cell may further comprise nucleic acid encoding a heterologous GDH activity.

Some embodiments of the process will proceed in a manner allowing for enzymatic co-factor recycling. In one aspect, the oxidized form of the enzymatic cofactor is NADP+ and the reduced form of said enzymatic cofactor is NADPH. In another aspect, the oxidized form of said enzymatic cofactor is NAD+ and the reduced form is NADH. Other co-factors useful in the process of the present invention include ATP, ADP, FAD and FMN.

In one embodiment, the process proceeds in an environment comprising organic solvents and in another, the process proceeds in an environment comprising long polymers.

The present invention also provides vectors and recombinant host cells comprising enzymatic activities which are used in the methods for producing the ASA intermediates. In one embodiment, the host cell comprises heterologous nucleic acid encoding GDH obtainable from species including including *T. acidophilum, Cryptococcus uniguttalatus* and Bacillus species and/or DKG reductase obtainable from Corynebacterium or Erwinia.

DETAILED DESCRIPTION OF THE PREFERRED EMBODIMENTS

Definitions

The following definitions apply as used herein to glucose (G); D-gluconate (GA); 2-keto-D-gluconate (2 KDG); 2,5-diketo-D-gluconate (2,5DKG or DKG), 2-keto-L-gulonic acid (2KLG, or KLG), L-idonic acid (IA), ascorbic acid (ASA), glucose dehydrogenase (GDH), gluconic acid dehydrogenase (GADH), 2,5-diketo-D-gluconate reductase (DKGR), and 2-keto-D-gluconate reductase (KDGDH).

As used herein, the term "non-fermentative" or "in vitro" refers to a biocatalytic process which exploits a cell's enzymatic activity. The cells may be non-viable or viable and not significantly growing. The cells may be genetically altered to eliminate their consumption of glucose and/or any intermediates produced. The in vitro process of the present invention encompasses the use of cell membranes which comprise enzymatic activity associated with the biocatalytic process, the use of permeabilized cells or lyophilized cells comprising the enzymatic activity associated with the biocatalytic process and the use of a host cell or host cell membranes or fragments in any form which provides the necessary enzymatic activity for the biocatalytic conversion of a carbon source to any of the ASA intermediates including but not limited to GA, KDG, DKG and KLG. The cell may be a recombinant cell which comprises heterologous nucleic acid encoding a desired enzymatic activity or a naturally occurring cell which comprises the desired enzymatic activity. The term "bioreactor" as used herein refers to the environment within which the non-fermentative or in-vitro process proceeds.

Many enzymes are only active in the presence of a co-factor, such as for example, NAD+ or NADP+. The term co-factor as used herein refers to a substrate secondary in nature to the enzymatic reaction, but vital to the enzymatic reaction. As used herein, the term "co-factor" includes, but is not limited to NAD+/NADH; NADP+/NADPH; ATP;

ADP, FAD/FADH$^2$ and FMN/FMNH$^2$. The phrase "regeneration of co-factor" or "recycling of co-factor" within the in vitro system refers to the phenomenon of continual oxidation and reduction of the required co-factor through biocatalysis, such that the required co-factor is present in the appropriate form for enzyme catalysis to take place. In the present invention, regeneration of co-factor provides an environment wherein a reduced form of a co-factor is available for a reducing enzyme and an oxidative form of the co-factor is available for an oxidation enzyme. The present invention encompasses regeneration of co-factor between any enzymatic oxidation step and any enzymatic reducing step in the biocatalytic pathway from carbon source to the ASA intermediate, e.g. KLG. The required co-factor may be present in catalytic amounts provided by the host cell environment or may be provided exogenously at the beginning of the bioreactor process in stochiometric quantities in either an oxidized or reduced form.

The amount of co-factor added exogenously to the bioreactor is between about 1 $\mu$M to about 5 mM and in a preferred embodiment, between about 5$\mu$M to about 1 mM. It has been discovered that ionic strength affects reductase activity. Therefore in a batch process wherein product accumulation produces increasing ionic strength, thereby reducing the activity of the reductase, it is preferred to have amounts of co-factor at the upper end of the range. In a continuous system wherein the product is removed, amounts of co-factor in the lower range may be added. A co-factor added exogenously to an in vitro system may be added alone or in combination with other substances associated with biocatalytic conversion of a carbon source to an ASA intermediate. The present process encompasses the use of co-factor immobilized to a carrier, co-factor chemically altered, such as in attachment to a long polymer, and to the use of co-factor in an isolated or purified form.

As used herein, the term carbon source encompasses suitable carbon sources ordinarily used by Enterobacteriaceae strains, such as 6 carbon sugars, including but not limited to glucose, gulose, sorbose, fructose, idose, galactose and mannose all in either D or L form, or a combination of 6 carbon sugars, such as sucrose, or 6 carbon sugar acids including but not limited to 2-keto-L-gulonic acid, idonic acid, gluconic acid, 6-phosphogluconate, 2-keto-D-gluconic acid, 5-keto-D-gluconic acid, 2-ketogluconatephosphate, 2,5-diketo-L-gulonic acid, 2,3-L-diketogulonic acid, dehydroascorbic acid, erythroascorbic acid and D-mannonic acid or the enzymatic derivatives of such as long as the carbon source is capable of being converted to an ASA intermediate such as, KDG, DKG and KLG, for example.

As used herein, the family "Enterobacteriaceae" refers to bacterial strains having the general characteristics of being gram negative and being facultatively anaerobic. Preferred Enterobacteriaceae strains are those that are able to produce 2,5-diketo-D-gluconic acid from D-glucose solutions. Included in the family of Enterobacteriaceae which are able to produce 2,5-diketo-D-gluconic acid from D-glucose solutions are the genus Erwinia, Enterobacter, Gluconobacter and Pantoea, for example. Intermediates in the microbial carbohydrate pathway from a carbon source to ASA, include but are not limited to GA, 2 KDG, 2,5DKG, 5DKG, 2KLG and IA. In the present invention, a preferred Enterobacteriaceae fermentation strain is a Pantoea species and in particular, *Pantoea citrea*. Four stereoisomers of ascorbic acid are possible: L-ascorbic acid, D-araboascorbic acid (erythorbic acid), which shows vitamin C activity, L-araboascorbic acid, and D-xyloascorbic acid. As used herein, the term, ASA intermediate encompasses any product in the pathway to ASA including but not limited to KDG, DKG and KLG.

As used herein, the term "recombinant" refers to a host cell that contains nucleic acid not naturally occurring in the organism and/or to host cells having additional copies or endogenous nucleic acid recombinantly introduced. The term "heterologous" as used herein refers to nucleic acid or amino acid sequences not naturally occurring in the host cell. As used herein, the term "endogenous" refers to a nucleic acid naturally occurring in the host.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof.

As used herein the term "mutation" refers to any alteration in a nucleic acid such that the product of that nucleic acid is inactivated or eliminated. Examples of mutations include but are not limited to point mutations, frame shift mutations and deletions of part or all of a gene encoding an enzymatic activity, such as an oxidative enzyme activity or a reducing activity. In one embodiment disclosed herein for producing KLG whereby co-factor is regenerated, nucleic acid encoding a membrane bound GDH activity is mutated thereby inactivating the GDH activity. In another embodiment, the 2-keto-D-gluconate dehydrogenase activity is inactivated thereby allowing for optimized production of the intermediate KDG.

The phrase "oxidative enzyme" as used herein refers to an enzyme or enzyme system which can catalyze conversion of a substrate of a given oxidation state to a product of a higher oxidation state than substrate. The phrase "reducing enzyme" refers to an enzyme or enzyme system which can catalyze conversion of a substrate of a given oxidation state to a product of a lower oxidation state than substrate. Oxidative enzymes associated with the biocatalysis of D-glucose to KLG include among others D-glucose dehydrogenase, D-gluconate dehydrogenase and 2-keto-D-gluconate dehydrogenase. Reducing enzymes associated with the biocatalysis of pathway intermediates of ASA into KLG include among others 2,5-diketo-D-gluconate reductase (DKGR), 2-keto reductase (2-KR) and 5-keto reductase (5-KR). Such enzymes include those produced naturally by the host strain or those introduced via recombinant means. In one embodiment disclosed herein, the process proceeds in a *Pantoea citrea* host cell having the naturally occurring membrane bound, non-NADP+ dependent GDH activity eliminated and a cytosolic NADP+ dependent GDH recombinantly introduced. In another embodiment, a heterologous nucleic acid encoding a reductase activity is introduced into the host cell. In a preferred embodiment, the reductase activity is obtainable from a Coryneform species or an Erwinia species. As used herein, the term "pathway enzyme" refers to any enzyme involved in the biocatalytic conversion of a carbon source to an ASA intermediate, e.g., KDG, DKG and KLG.

The terms "isolated" or "purified" as used herein refer to a nucleic acid or protein or peptide or co-factor that is removed from at least one component with which it is naturally associated. In the present invention, an isolated nucleic acid can include a vector comprising the nucleic acid.

It is well understood in the art that the acidic derivatives of saccharides, may exist in a variety of ionization states depending upon their surrounding media, if in solution, or out of solution from which they are prepared if in solid form. The use of a term, such as, for example, idonic acid, to designate such molecules is intended to include all ionization states of the organic molecule referred to. Thus, for example, "idonic acid", its cyclized form "idonolactone", and "idonate" refer to the same organic moiety, and are not intended to specify particular ionization states or chemical forms.

DETAILED DESCRIPTION

The present invention relates to the biocatalytic production of ASA intermediates, e.g., KDG, DKG and KLG, from a carbon source in an in vitro or non-fermentative environment. Depending upon the intermediate being produced, the process may require the presence of enzymatic co-factor. In a preferred embodiment disclosed herein, the enzymatic co-factor is regenerated. Due to the cost of co-factor, it is highly advantageous to employ an in vitro process which allows for the regeneration of catalytic amounts of co-factor provided by the host cell environment or provided exogenously.

Non-Fermentative Production of ASA intermediates

The present invention provides a means for the production of ASA intermediates. Such intermediates can be further processed to ASA, ASA stereoisomers or other products such as erythorbate. In one preferred embodiment, KDG is the desired ASA intermediate produced, the bioreactor is provided with viable or non-viable *Pantoea citrea* host cells having a mutation in a gene encoding 2-keto-D-gluconate dehydrogenase activity as described herein in Example II. In this embodiment, the carbon source is biocatalytically converted through at two oxidative steps, see FIG. 2, to KDG. In this embodiment, there is no need for co-factor regeneration.

Figure 2:
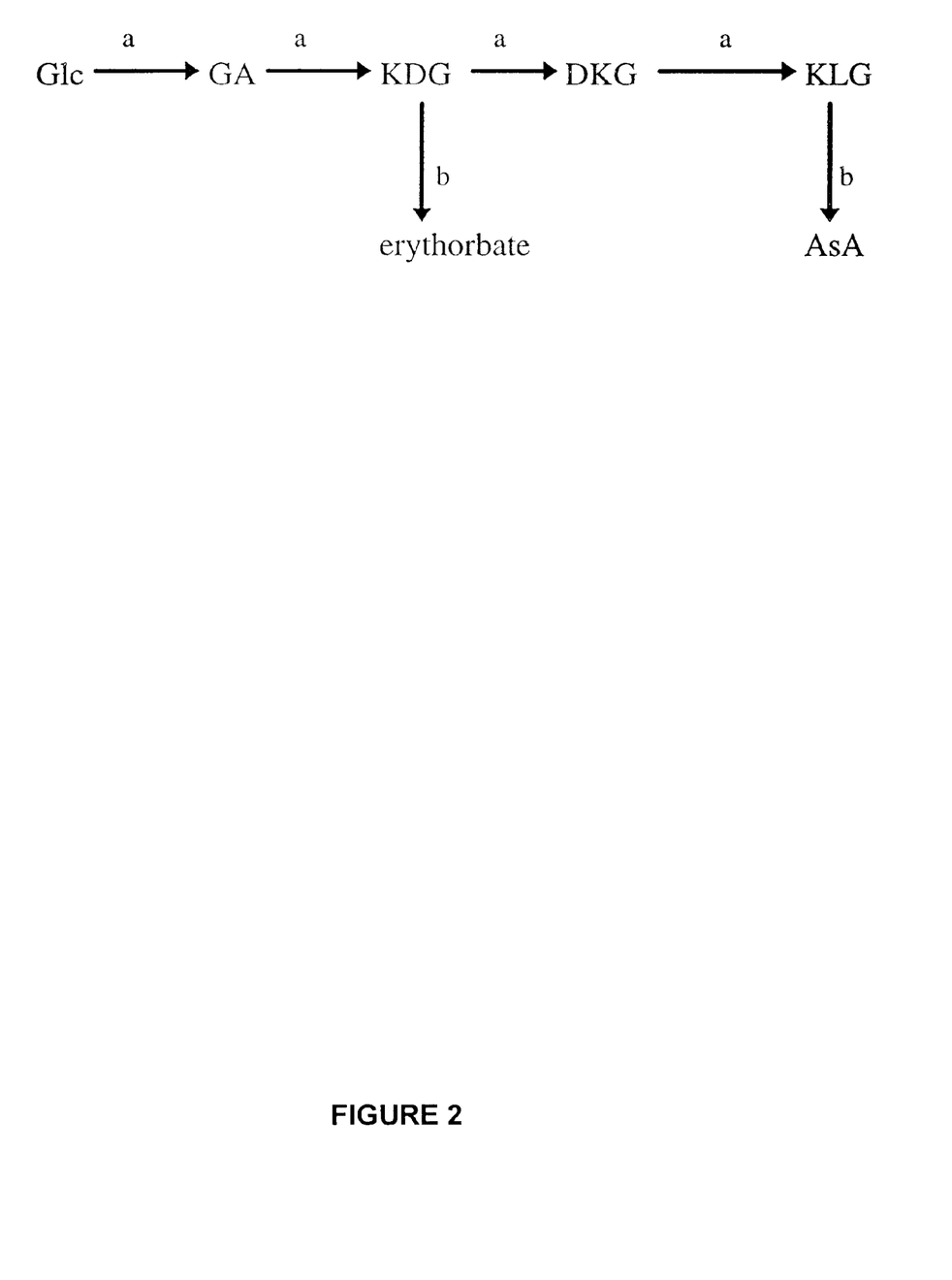
FIG. 2 is a schematic representation of a pathway to ASA intermediates. Steps labeled A are enzymatic; steps labeled B are either enzymatic or chemical conversions. The enzyme that converts glucose (Glc) to GA is a GDH activity; the oxidative enzyme that converts GA to KDG is a GADH activity; the oxidative enzyme that converts KDG to DKG is a KDGDH activity and the reducing enzyme that converts DKG to KLG is DKGR activity.

When DKG is the desired ASA intermediate, the bioreactor is provided with viable or non-viable *Pantoea citrea* host cells and a carbon source which is biocatalytically converted through three oxidative steps, see FIG. 2, to DKG. In this embodiment, there is not need for co-factor regeneration.

When KLG is the desired ASA intermediate, the bioreactor is provided with viable or non-viable *Pantoea citrea* host cells and a carbon source, such as glucose, which is biocatalytically converted through three oxidative steps, as shown in FIG. 2 and one reducing step to KLG. In this embodiment, the reductase activity may be encoded by nucleic acid contained within the *Pantoea citrea* host cell or provided exogenously. In this embodiment, the first oxidative enzymatic activity requires an oxidized form of the co-factor and the reducing enzymatic activity requires a reduced form of co-factor. In a preferred embodiment disclosed herein, the *Pantoea citrea* cell is modified to eliminate the naturally occurring GDH activity and a heterologous GDH obtainable from *T. acidophilum, Cryptococcus uniguttalatus* or Bacillus species and having a specificity for NADPH+ is introduced into the Pantoea cell in order to provide a co-factor recycling system which requires and regenerates one co-factor. This embodiment, provides a means for co-factor regeneration, thereby eliminating the cost of continuously adding exogenous co-factor to the bioreactor for the production of KLG in Pantoea cells. In this embodiment, the host cell further comprises nucleic acid encoding a 2,5-DKG reductase activity or the 2,5-DKG reductase is added exogenously to the bioreactor.

In another embodiment for making KLG, the bioreactor is charged with *Pantoea citrea* cells comprising nucleic acid encoding membrane-bound GDH, appropriate enzymes and cofactor, and gluconic acid is added which is converted to DKG. The reaction mixture is then made anaerobic and glucose is added. The GDH converts the glucose to GA, and the reductase converts DKG to KLG, while cofactor is recycled. When these reactions are completed, oxygen is added to convert GA to DKG, and the cycles continue.

In vitro Biocatalytic Environment

A biocatalytic process of converting a carbon source to an ASA intermediate begins with a suitable carbon source used by Enterobacteriaceae strains, such as a 6 carbon sugar, including for example, glucose, or a 6 carbon sugar acid, such as for example, KDG. Other metabolite sources include, but are not limited to galactose, lactose, fructose, or the enzymatic derivatives of such. In addition to an appropriate carbon source, media must contain suitable minerals, salts, cofactors, buffers and other components known to those of skill in the art for sustaining cultures and promoting the enzymatic pathway necessary for production of desired end-products. The cells are first grown and for the non-fermentative process the carbon source utilized for growth is eliminated, the pH is maintained at between about pH 4 and about pH 9 and oxygen is present.

In the in vitro biocatalytic process, the carbon source and metabolites thereof proceed through enzymatic oxidation steps or enzymatic oxidation and enzymatic reducing steps which may take place outside of the host cell intracellular environment and which exploit the enzymatic activity associated with the host cell and proceed through a pathway to produce the desired ASA intermediate. The enzymatic steps may proceed sequentially or simultaneously within the bioreactor and some have a co-factor requirement in order to produce the desired ASA intermediate. The present invention encompasses an in vitro process wherein the host cells are treated with an organic substance, as described in Example III, such that the cells are non-viable, yet enzymes remain available for oxidation and reduction of the desired carbon source and/or metabolites thereof in the biocatalysis of carbon source to ASA intermediate. The present invention also encompasses an in vitro process wherein the host cells are lyophilized, permeabilized by any means, spray-dried, fractured or otherwise treated such that the enzymes are available for the conversion of carbon source to ASA intermediate.

The oxidative or reducing enzymatic activities may be bound to a host cell membrane, immobilized, such as to a resin, for example AminoLink coupling gel (from Pierce Chemical Co), to a polymer, or soluble in the bioreactor environment. In a preferred embodiment, at least one oxidative enzyme is membrane bound. The environment may proceed in an organic or aqueous system or a combination of both, and may proceed in one vessel or more. In one embodiment, the process proceeds in two vessels, one which utilizes oxygen and one which is anaerobic. For example, the membrane bound enzymes that require oxygen (GDH, GADH, KDGDH) may be isolated from those enzymes that do not require oxygen (cofactor dependent GDH, cofactor dependent DKGR) allowing the use of a smaller volume containment vessel that requires oxygen, thereby reducing cost. The bioreactor may be performed in batch or in a continuous process. In a batch system, regardless of what is added, all of the broth is harvested at the same time. In a continuous system, the broth is regularly removed for downstream processing while fresh substrate is added. The intermediates produced may be recovered from the fermentation broth by a variety of methods including ion exchange resins, absorption or ion retardation resins, activated carbon, concentration-crystallization, passage through a membrane, etc.

The bioreactor process may also involve more than one cell type, e.g., one cell may comprise the oxidative activities and a second cell may comprise the reducing activities. In another embodiment, the host cell is permeabilized or lyophilized (Izumi et al., *J. Ferment. Technol.* 61 (1983) 135–142) as long as the necessary enzymatic activities remain available to convert the carbon source or derivatives thereof. The bioreactor may proceed with some enzymatic activities being provided exogenous and in an environment wherein solvents or long polymers are provided which stabilize or increase the enzymatic activities. In an embodiment disclosed herein, methanol or ethanol is used to increase reductase activity. In another embodiment, Gafquat is used to stabilise the reductase (see Gibson et al., U.S. Pat. No. 5,240,843).

In one illustrative bioreactor described herein, the host cell is a permeabilized *Pantoea citrea* provided D-glucose as a carbon source which undergoes a series of oxidative steps through enzymatic conversions. The oxidizing enzymes include GDH, GADH and DGDH and a reducing step which involves 2 DKGR (see U.S. Pat. No. 3,790,444) to yield KLG. The KLG produced by a process of the present invention may be further converted to ascorbic acid and the KDG to erythorbate by means known to those of skill in the art, see for example, Reichstein and Grussner, Helv. Chim. Acta., 17, 311–328 (1934).

Co-Factor Regeneration

One of the advantages of the process of the present invention lies in the regeneration of co-factor required by pathway enzymes. Examples of cofactor which can be used in the current process include but are not limited to NAD+/NADH; NADP+/NADPH; ATP; ADP, $FAD/FADH^2$ and $FMN/FMNH^2$.

Figure 1:
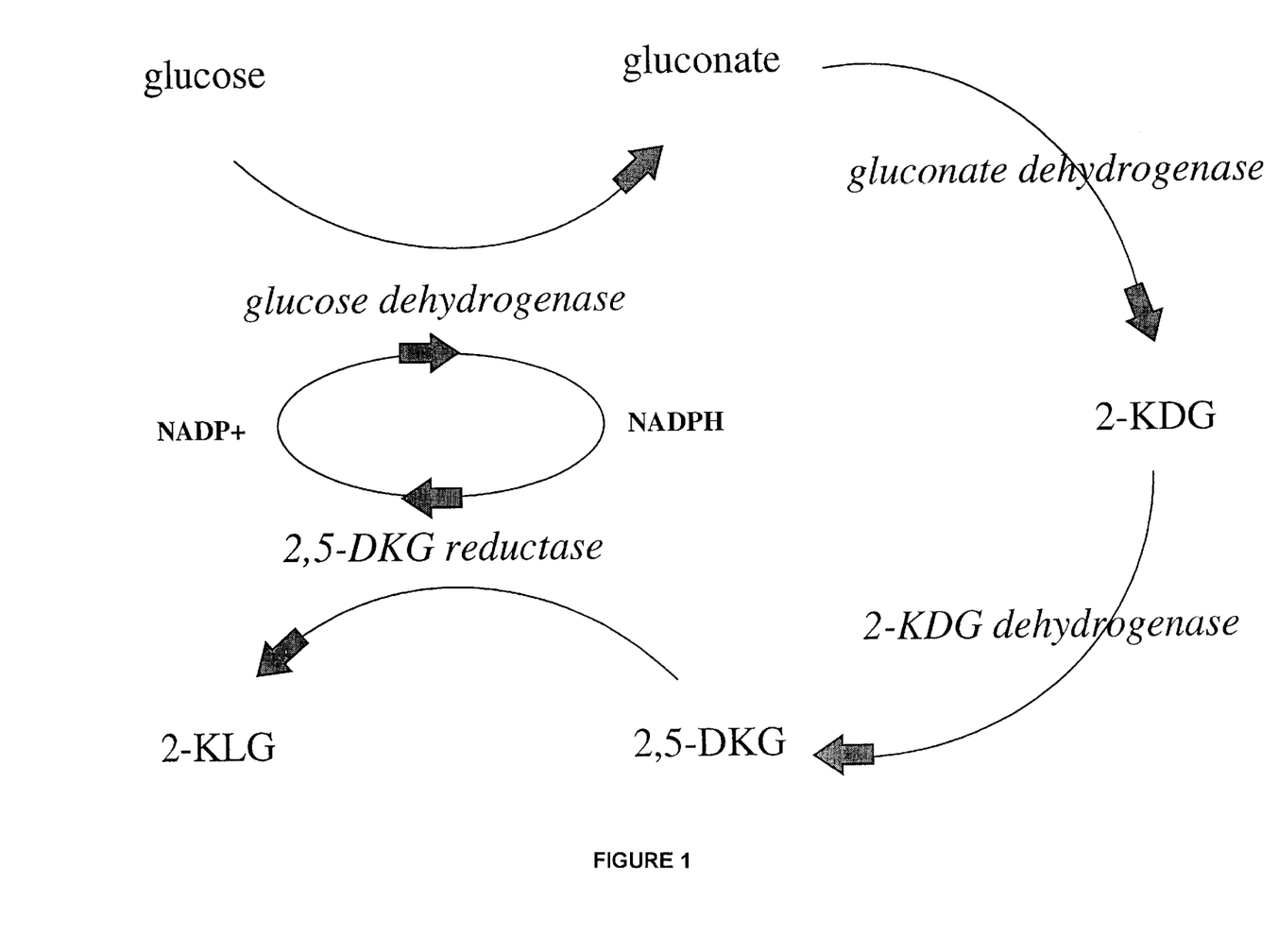
FIG. 1 is a schematic representation of an in vitro process wherein NADP+ and NADPH are recycled between oxidation and reduction steps.

In one embodiment of the invention, a carbon source is converted to KLG in a process which involves co-factor regeneration, as shown in FIG. 1. In this enzymatic cofactor regeneration process, one equivalent of D-glucose is oxidized to one equivalent of D-gluconate, and one equivalent of NADP+ is reduced to one equivalent of NADPH by the catalytic action of GDH. The one equivalent D-gluconate produced by the GDH is then oxidized to one equivalent of 2-KDG, and then to one equivalent of 2,5-DKG by the action of membrane bound dehydrogenases GADH and KDGDH, respectively. The one equivalent 2,5-DKG produced is then reduced to one equivalent of 2-KLG, and the NADPH is oxidized back to one equivalent of NADP+ by the action of 2,5-DKG reductase, effectively recycling the equivalent cofactor to be available for a second equivalent of D-glucose oxidation. Other methods of cofactor regeneration can include chemical, photochemical, and electrochemical means, where the equivalent oxidized NADP+ is directly reduced to one equivalent of NADPH by either chemical, photochemical, or electrochemical means.

Recombinant Methods

Host Cells

Any oxidative or reducing enzymes necessary for directing a host cell carbohydrate pathway into ASA intermediates, such as, for example, KDG, DKG or KLG, can be introduced via recombinant DNA techniques known to those of skill in the art if such enzymes are not naturally occurring in the host cell. Alternatively, enzymes that would hinder a desired pathway can be mutated by recombinant DNA methods. The present invention encompasses the recombinant introduction or mutation of any enzyme or intermediate necessary to achieve a desired pathway.

In one embodiment of the present invention a carbon source, such as glucose, is converted to KLG through multiple oxidation steps and a reducing step. In this embodiment, the first oxidation step and the reducing step requires co-factor. The host cell is *Panoea citrea*, the naturally occurring nucleic acid encoding glucose dehydrogenase (GDH) is mutated such that the dehydrogenase activity is eliminated and a heterologous GDH is introduced into the cell. The present invention encompasses a host cell having additional mutation of enzymes in the carbon flow pathway which affect production. For general techniques, see, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing "Associates and Wiley Interscience, N.Y.

In one embodiment of the present invention, nucleic acid encoding DKG reductase (DKGR) is recombinantly introduced into the Pantoea fermentation strain. Many species have been found to contain DKGR, particularly members of the Coryneform group, including the genera Corynebacterium, Brevibacterium, and Arthrobacter. In one embodiment of the present invention, 2,5-DKGR obtainable from Corynebacterium sp. strain SHS752001 (Grindley et al., 1988, *Applied and Environmental Microbiology* 54: 1770–1775) is recombinantly introduced into a *Pantoea citrea*. In another embodiment, 2,5 DKG reductase obtainable by Erwinia herbicola is disclosed in U.S. Pat. No. 5,008,193 to Anderson et al.

Sources for nucleic acid encoding oxidative or reducing enzymes include the following:

| ENZYME | CITATION |
| --- | --- |
| glucose dehydrogenase | Smith et al. 1989, Biochem. J. 261:973; Neijssel et al. 1989, Antonie Van Leauvenhoek 56(1):51–61 |
| gluconic acid dehydrogenase | Matsushita et al. 1979, J. Biochem. 85:1173; Kulbe et al. 1987, Ann. N.Y. Acad Sci 506:552 |
| 2-keto-D-gluconic acid dehydrogenase | Stroshane 1977 Biotechnol. BioEng 19(4) 459 |
| 2-keto gluconate reductase | J. Gen. Microbiol. 1991, 137:1479 |
| 2,5-diketo-D-gluconic acid reductase | U.S. Pat. Nos.: 5,795,761; 5,376,544; 5,583,025; 4,757,012; 4,758,514; 5,008,193; 5,004,690; 5,032,514 |

Vector Sequences

Expression vectors used in expressing the pathway enzymes, e.g., a dehydrogenase or reductase, of the present process in host microorganisms comprise at least one promoter associated with the enzyme, which promoter is functional in the host cell. In one embodiment of the present invention, the promoter is the wild-type promoter for the selected enzyme and in another embodiment of the present invention, the promoter is heterologous to the enzyme, but still functional in the host cell. In one embodiment of the present invention, nucleic acid encoding the enzyme is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the host microorganism which allows for ease of selection of those hosts containing the vector. Examples of such selectable markers include but are not limited to antibiotics, such as, erythromycin, actinomycin, chloramphenicol and tetracycline.

A preferred plasmid for the recombinant introduction of non-naturally occurring enzymes or intermediates into a strain of Enterobacteriaceae is RSF1010, a mobilizable, but not self transmissible plasmid which has the capability to replicate in a broad range of bacterial hosts, including Gram− and Gram+ bacteria. (Frey et al., 1989, The Molecular biology of IncQ plasmids. In: Thomas (Ed.), *Promiscuous Plasmids of Gram Negative Bacteria*. Academic Press, London, pp. 79–94). Frey et al. (1992, Gene 113:101–106) report on three regions found to affect the mobilization properties of RSF1010.

Transformation

General transformation procedures are taught in Current Protocols In Molecular Biology (vol. 1, edited by Ausubel et al., John Wiley & Sons, Inc. 1987, Chapter 9) and include calcium phosphate methods, transformation using DEAE-Dextran and electroporation. A variety of transformation procedures are known by those of skill in the art for introducing nucleic acid encoding a pathway enzyme in a given host cell. The present process encompasses pathway enzymes produced by and purified from recombinant host cells and added exogenously into the in vitro environment as well processes wherein the pathway enzyme, either heterologous or endogenous to the host cell, is expressed by an actively growing host cell or present in the membrane of a non-viable host cell. A variety of host cells can be used for recombinantly producing the pathway enzymes to be added exogenously, including bacterial, fungal, mammalian, insect and plant cells. Plant transformation methods are taught in Rodriquez (WO 95/14099, published May 26, 1995).

In a preferred embodiment of the process, the host cell is an Enterobacteriaceae. Included in the group of Enterobacteriaceae are Erwinia, Enterobacter, Gluconobacter and Pantoea species. In the present invention, a preferred Enterobacteriaceae fermentation strain is a Pantoea species and in particular, *Pantoea citrea*. In another preferred embodiment, the host cell is *Pantoea citrea* comprising pathway enzymes capable of converting a carbon source to KLG. The present invention encompasses pathways from carbon source to KLG through any intermediate in the microbial carbohydrate pathway capable of using a carbon source to produce KLG, going through intermediates including but not limited to GA, 2 KDG, 2,5DKG, 5DKG, and IA. In one embodiment, nucleic acid encoding the pathway enzyme is introduced via a plasmid vector and in another embodiment, nucleic acid encoding a pathway enzyme is stably integrated into the host cell genome.

Identification of Transformants

Whether a host cell has been transformed can be detected by the presence/absence of marker gene expression which can suggest whether the nucleic acid of interest is present However, its expression should be confirmed. For example, if the nucleic acid encoding a pathway enzyme is inserted within a marker gene sequence, recombinant cells containing the insert can be identified by the absence of marker gene function. Alternatively, a marker gene can be placed in tandem with nucleic acid encoding the pathway enzyme under the control of a single promoter. Expression of the marker gene in response to induction or selection usually indicates expression of the enzyme as well.

Alternatively, host cells which contain the coding sequence for a pathway enzyme and express the enzyme may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

Additionally, the presence of the enzyme polynucleotide sequence in a host microorganism can be detected by DNA-DNA or DNA-RNA hybridization or amplification using probes, portions or fragments of the enzyme polynucleotide sequences.

Assay Conditions

Methods for detection of ASA intermediates, ASA and ASA sterioisomers include the use of redox-titration with 2,6 dichloroindophenol (Burton et al. 1979, J. Assoc. Pub. Analysts 17:105) or other suitable reagents; high-performance liquid chromatography (HPLC) using anion exchange (J. Chrom. 1980, 196:163); and electro-redox procedures (Pachia, 1976, Anal. Chem. 48:364). The skilled artisan will be well aware of controls to be applied in utilizing these detection methods.

Recovery of Intermediates

Once produced, the ASA intermediates can be recovered and/or purified by any means known to those of skill in the art, including, lyophilization, crystallization, spray-drying, etc. The intermediates can also be formulated directly from the bioreactor and granulated or put in a liquid formulation.

The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

EXAMPLES

Example I

This example describes the method for producing a *Pantoea citrea* host cell having a mutation in the naturally occurring GDH.

Cloning of Glucose Dehydrogenase Gene (GDH) from *Pantoea citrea*

The glucose dehydrogenase gene was cloned by polymerase chain reaction (PCR). Two primers were used in the PCR: 5'AGGGAGTGCTTACTACCTTATCTGCGG-TATA3' (SEQ ID NO;1) and 5'CGCTAGCTGTGCAATC-CATTGATTTTGCACA3' (SEQ ID NO;2). After the PCR, a DNA product of about 2 kb was cloned in the vector, pGEM-T (Promega), and the recombinant *E. coli* with the correct DNA insert was identified and the clone was desigated as pRL. The DNA insert was analyzed by DNA sequencing and its sequence was found to be 60–70% identical to the published DNA sequences of a GDH of a strain of *Pantoea citrae*.

Generation of a Deleted GDH Gene by the Insertion of Chloramphenicol Resistance Gene To generate the deletion mutant of the GDH gene in *Pantoea citrea*, a recombinant copy of the gene to be deleted was first generated by the introduction of a selectable marker, chloramphenicol resistance gene (CAT). The in vitro generated copy was introduced into the *Pantoea citrae* and allowed to recombine with the wild-type copy through homologous recombination. The pRL DNA was then analyzed by digestion with various restriction enzymes. Two SmaI cleavage sites located about 700 bp apart within the GDH encoding DNA were found. The pRL was digested with SmaI to remove the 700 bp fragment which was then replaced with a SmaI digested 1.05 kb DNA containing the chloramphenicol resistance gene to generate the recombinant plasmid, designated as pRLcm4. The method used to generate pRLcm4 were standard techniques used by those of skill in the art. The GDH-CAT encoding sequence from pRLcm4 was further transferred to a plasmid, pGP704. The DNA encoding the GDH-CAT cassette was removed from pRLcm4 by the combined digestion of restriction enzymes AatII and SpeI. The cohesive ends of the digested DNA were removed by the treatment of T4 DNA polymerase in the presense of deoxynucleotide triphosphate mixtures. The GDH-CAT cassette was then ligated with the EcoRV digested pGP704. Recombinant plasmid of pGP704 containing the GDH-CAT cassette was identified and designated as p704RLcm.

Introduction of the Deleted GDH Gene into the Chromosome of Pantoea citrae:

Plasmid p704RLcm was introduced into wild-type Pantoea citrae by electroporation. The transformed cell was first plated in agar plates containing 12.5 ug/ml of chloramphenicol and resistant colonies were observed. To differentiate the true deletion mutant (which should display chloramphenicol resistant phenotype) from cells which simply harbors the plasmid p704RLcm, the chloramphenicol resistant colonies were screened against ampicillin, another antibiotic resistance marker carrier by p704RLcm. Amplicilin sensitve clones were identified. Several clones which had the right phenotype (chloramphenicol resistant and amplicilin sensitive) were characterized by biochemical assays and all exhibited GDH negative phenotype. DNA blot analysis also confirmed that the wild-type GDH gene was replaced with the deleted copy.

Example II

Example II describes the method for producing a host cell having a mutation in the naturally occurring 2-Keto-D-gluconate dehydrogenase (E3).

2-Keto-D-gluconate dehydrogenase (EC1.1.99.4) from *Gluconobacter melanogenus* is purified according to the procedure of McIntire et al., (McIntire, W., Singer, T. P., Ameyama, M., Adachi, O., Matsushita, K., and Shinagawa, E. *Biochem. J.* (1985) 231, 651–654) and references therein. The purified protein is digested with *J.* (1985) 231, 651–654) and references therein. The purified protein is digested with trypsin and chymotrypsin or other proteases to produce peptide fragments which are separated by HPLC or other techniques. Individual peptides are collected and sequenced. From the sequence, DNA probes are synthesized which will anneal to the corresponding sequence in the host organism or a related organism's genome. Using standard PCR techniques, larger fragments of the desired gene are amplified, purified and sequenced. These fragments are used to hybridize to the gene and allow for cloning and sequencing of the entire gene. Once the sequence is known, the gene is deleted as described for glucose dehydrogenase (GDH) in Example 1.

Other methods to reduce or eliminate 2-keto-D-gluconate dehydrogenase include inhibitors (organic acids such as citrate and succinate are reported to inhibit 2-keto-D-gluconate dehydrogenase; Shinagawa, E. and Ameyama, M. *Methods in Enzymology* (1982) 89, 194–198), and changes in pH or temperature.

The enzyme can be assayed for activity or loss of activity using the assays described in Shinagawa and Ameyama.

Example III

Example III illustrates a method for producing KLG in Bioreactor where co-factor is regenerated.

Materials and Methods

Cell Permeabilization 400 ml of *P. citrea* cells having a mutation in the naturally occurring membrane bound GDH was grown to 80 OD (600 nm) in 10 g/L gluconate, and mixed with 16 ml of a mixture of 10% toluene and 90% acetone for 3 minutes at 22 C. The permeabilized cells were then centrifuged for 10 minutes at 9000 rpm, and the resulting cell pellet was washed with 400 ml of 50 mM tris, pH 7. The washings were repeated twice more to ensure removal of residual organic solvent.

Charging of the Reactor

The 400 ml of permeabilized cells in 50 mM tris, pH 7 from above were placed into a one liter glass vessel equipped with a stirrer, temperature control, oxygen delivery tube, base delivery tube, a sample port, and oxygen and pH probes. 200 ul of MAZU antifoam (BASF) was added to the solution to control excess foaming, pressurized air was fed to the vessel, the temperature was brought to 28 C, and the stirrer was turned on to rotate at 1200 rpm until the oxygen probe read over 60% saturation. 16 grams of crystalline glucose and 4 grams of crystalline Na gluconate were then added to a final concentration of 10 g/L gluconate and 40 g/L glucose. The mixture was allowed to react until all the gluconate had been converted to DKG. The glucose level was maintained above 20 g/L. Due to the cell permeabilization, minimal amounts of glucose entered into non-productive cellular metabolism. pH was maintained at 7 by the controlled addition of 50% NaOH throughout.

Addition of the Soluble Enzymes and Cofactor

Once the gluconate was converted to DKG, 2000 units each of cofactor dependent GDH and DKG reductase (for DKGR, one unit is equal to one OD absorbance change per minute when measured at 340 nm) were added, along with 400 uM NADP+. The reactor was stirred, fed air, and maintained at 28 C as above. Periodic additions of glucose were made throughout the run to ensure constant substrate supply for both of the cofactor dependent enzymes.

Results

A bioreactor experiment was performed with non-purified reductase A:F22Y/A272G (U.S. Pat. No. 5,795,761), in the form of a crude extract from *E. coli. T. acidophilum* GDH and NADP+ were purchase in purified form from Sigma. GA to DKG rates were greater than 10 g/L/hr. Initial 2KLG formation rates were greater than 10 g/L/hr. Integrated rate over the first six hours was over 5 g/L/hr. Cofactor appeared to be stable over the first 6 hours, and predominantly in the reduced form. The total turnover number was 537 (215 mM 2KLG/0.4 mM NADP+). During the first six hours, the intermediates GA and DKG never went above 4 g/L. The run was stopped 6.5 hours after the initial cell charge, and a wind down phase of low agitation at 22 C was run overnight. The final titer of KLG was about 42 g/L.

Aliquots were removed during the course of the bioreactor incubation. These aliquots were first spun in a microfuge to pellet the cells. To assay for remaining reductase activity, 25 microliters of sample supurnatant were added to a solution composed of 910 ul buffer (50 mM bis-tris, pH 7), 20 ul DKG (70 mg/ml) and 250 uM NADPH. Reductase activity was measured by monitoring the loss of absorbance at 340 nm for 1 min. GDH activity was measured by adding 25 ul of sample to a solution containing 520 ul buffer, 150 ul NaCl (1 M), 200 ul urea (8 M), 50 ul glc (1 M) and 60 ul NADP+ (5 mM), and monitoring increase in absorbance at 340 nm for 1 min. Both the reductase and the GDH showed full activity throughout the course of the bioreactor experiment.

Example IV

This Example illustrates the production of KDG in an in-vitro bioreactor.

Cells containing membrane-bound D-glucose dehydrogenase and D-gluconic acid dehydrogenase activities but not 2-keto-D-gluconate dehydrogenase activity are grown and harvested. One example of such a cell is *Pantoea citrea* which has a mutation in the 2-keto-D-gluconate dehydrogenase enzyme, and is grown and treated as in Example 1II. The cells are permeabilized as described in Example III. Glucose (crystalline or in solution) is added in aliquots or continuously. The pH is maintained by controlled addition of a concentrated NaOH solution. The glucose is converted to D-gluconic acid and then KDG. Product formation is monitored by analyzing aliquots on a suitable HPLC system. Product is recovered by removing the cells by centrifugation and concentrating or removing the remaining liquid.

Example V

This example illustrates that the addition of organic solvents increases reductase activity.

Figure 3:
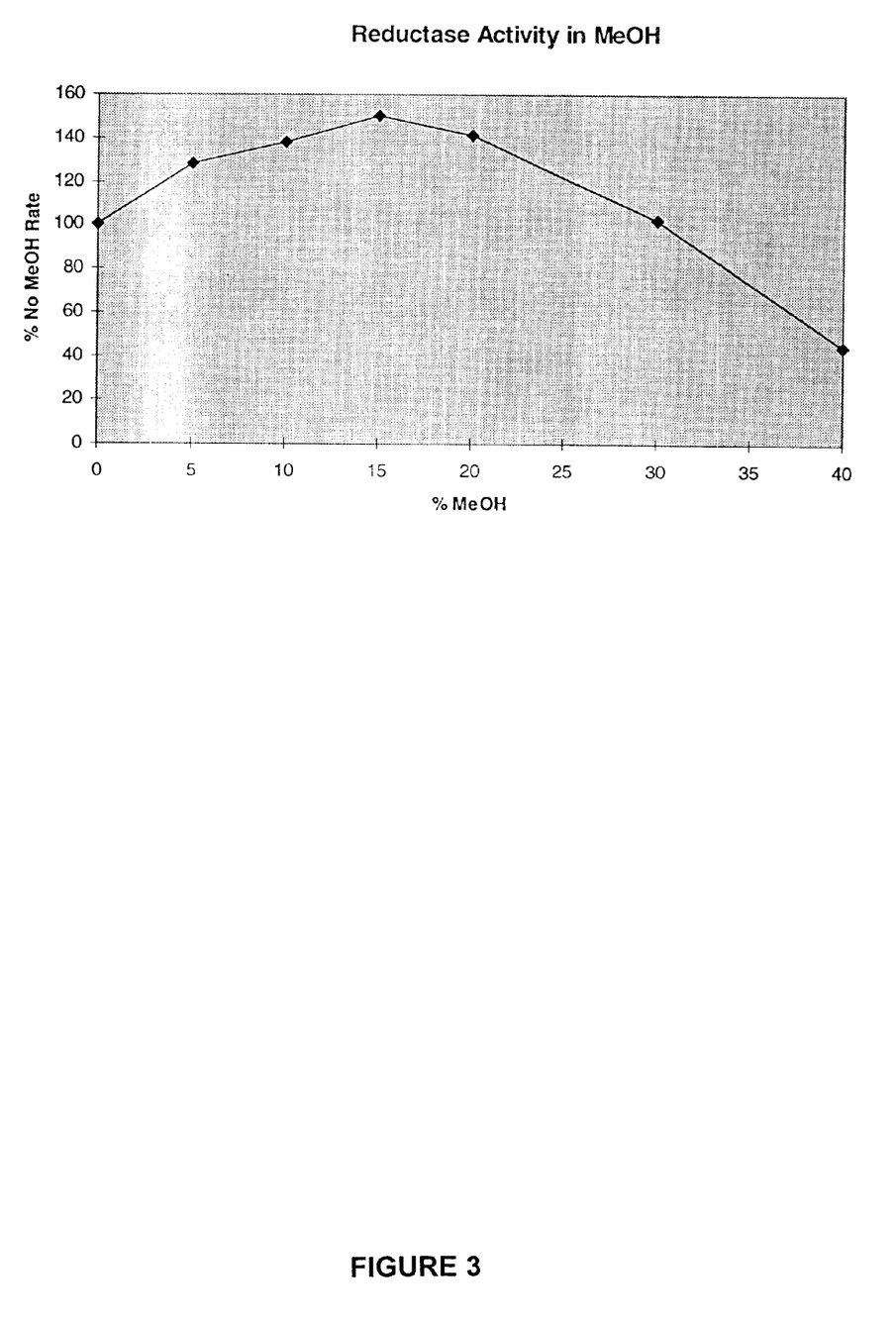
FIG. 3 illustrates the activity of reductase in the presence of 0–40% methanol at pH 7 and 30° C.
Figure 4:
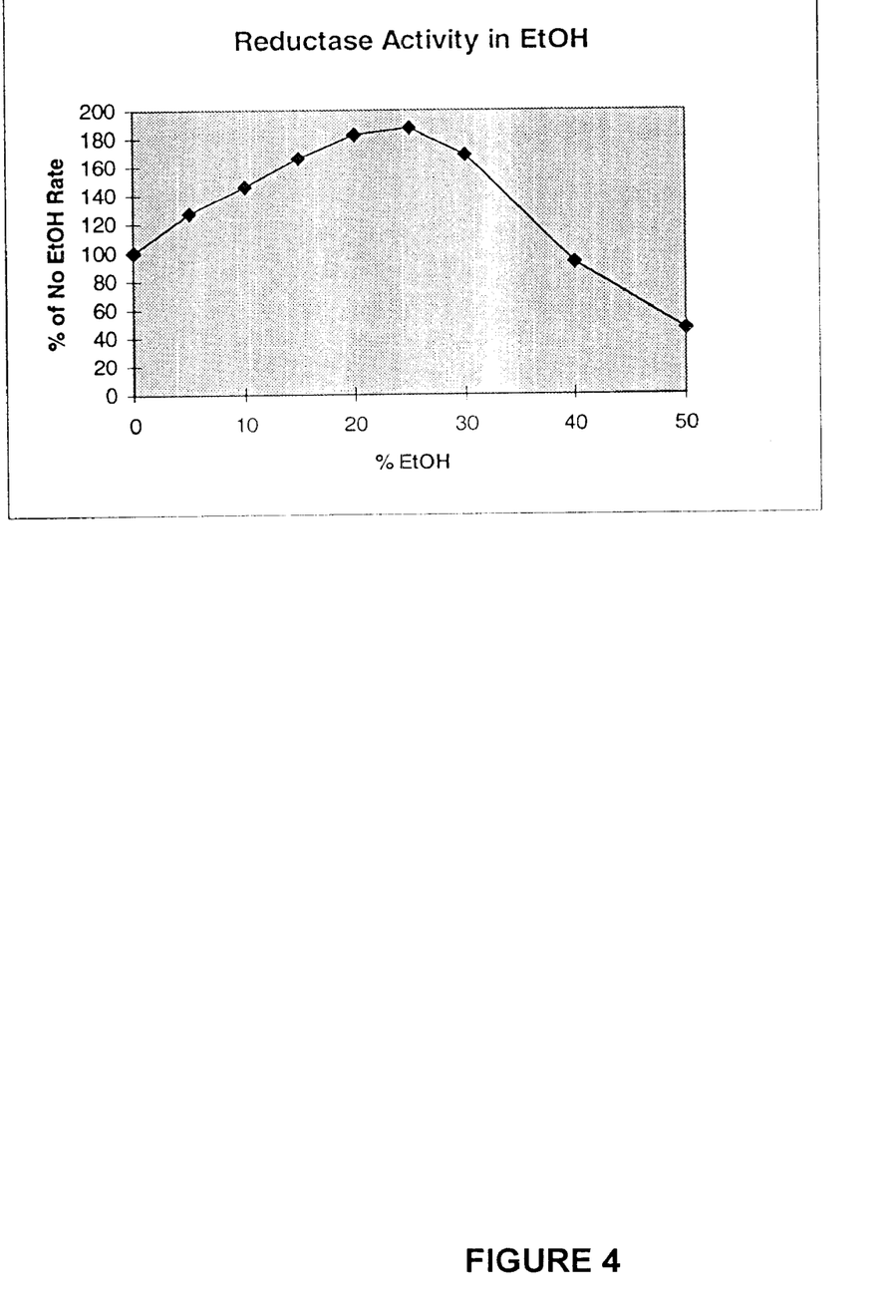
FIG. 4 illustrates Reductase activity in the presence of 0–50% ethanol at pH 7 and 22° C.

1–2 mg of DKG, 250 uM NADPH, F22Y/A272G reductase A and enough 50 mM bis-tris buffer, pH 7, to bring the final volume to 1 ml is added to a cuvette. Reductase activity is measured by monitoring the decrease in absorbance at 340 nm. The amount of reductase added typically produces a change in absorbance of 0.1–0.2 OD/min at room temperature or 30° C. Under the same conditions, aliquots of methanol or ethanol were added to the solution and reductase activity measured. Reductase activity in the presence of various amounts of methanol at 30° C. is shown in FIG. 3, and activity in the presence of ethanol at 22° C. is shown in FIG. 4.

As shown in the Figures, reductase activity is increased in the presence of certain amounts of methanol or ethanol. Optimal concentrations range between 10 and 25% of the organic solvent.

GDH from *T. acidophilum* has a small decrease in activity when it is incubated with 10% methanol (assay conditions are 50 mM Tris, pH 7, 12.5 mM D-glucose, 250 uM NADP+, in 1 ml. Activity is monitored by the increase in absorbance at 340 nm). Permeabilized cells were incubated with 15% MeOH and gluconic acid. The activities of D-gluconic acid dehydrogenase and 2-keto-D-gluconic acid dehyrogenase were not significantly affected by the addition of methanol as monitored by product formation (HPLC analysis).

The addition of methanol or ethanol to a complete bioreactor reaction would increase reductase activity. Losses in the GDH activity or other components could be overcome by adding more GDH or cells.

Example VI

Example VI illustrates the reductase activity in the presence of Gafquat and PEG8000.

Reductase was incubated with 250 uM NADPH, 1–2 mg/ml DKG, and 0, 0.7% and 2.8% Gafquat (ISP Technologies, Inc.) or 0.5% PEG8000 in 1 ml (50 mM bis-tris buffer, pH 7) at 30° C. Reductase activity was measured as in Example VI. As shown in Table 1, the addition of Gafquat increases reductase activity by 80% compared to activity without Gafquat. PEG8000 increases reductase activity approximately 15%.

TABLE 1

Increase of reductase activity in the presence of Gafquat or PEG8000.

| Polymer | % Added to Final Solution | % Activity with No Additive |
|---|---|---|
| Gafquat | 0.7–2.8 | 180 |
| PEG8000 | 0.5 | 115 |

Example VII

Example VII illustrates the reductase activity in the presence of salt.

Reductase A F22Y/A272G activity was measured in the presence of varying amounts of different salts. The assay consisted of adding reductase to a solution (1 ml final volume) containing 250 uM NADPH, DKG (1–1.5 mg/ml), 50 mM bis-tris buffer, pH 7.0, and varying amounts of potassium phosphate, NaCl, KCl or CaCl2. All reactions were done at 30° C. The results are shown in FIG. 5.

Figure 5:
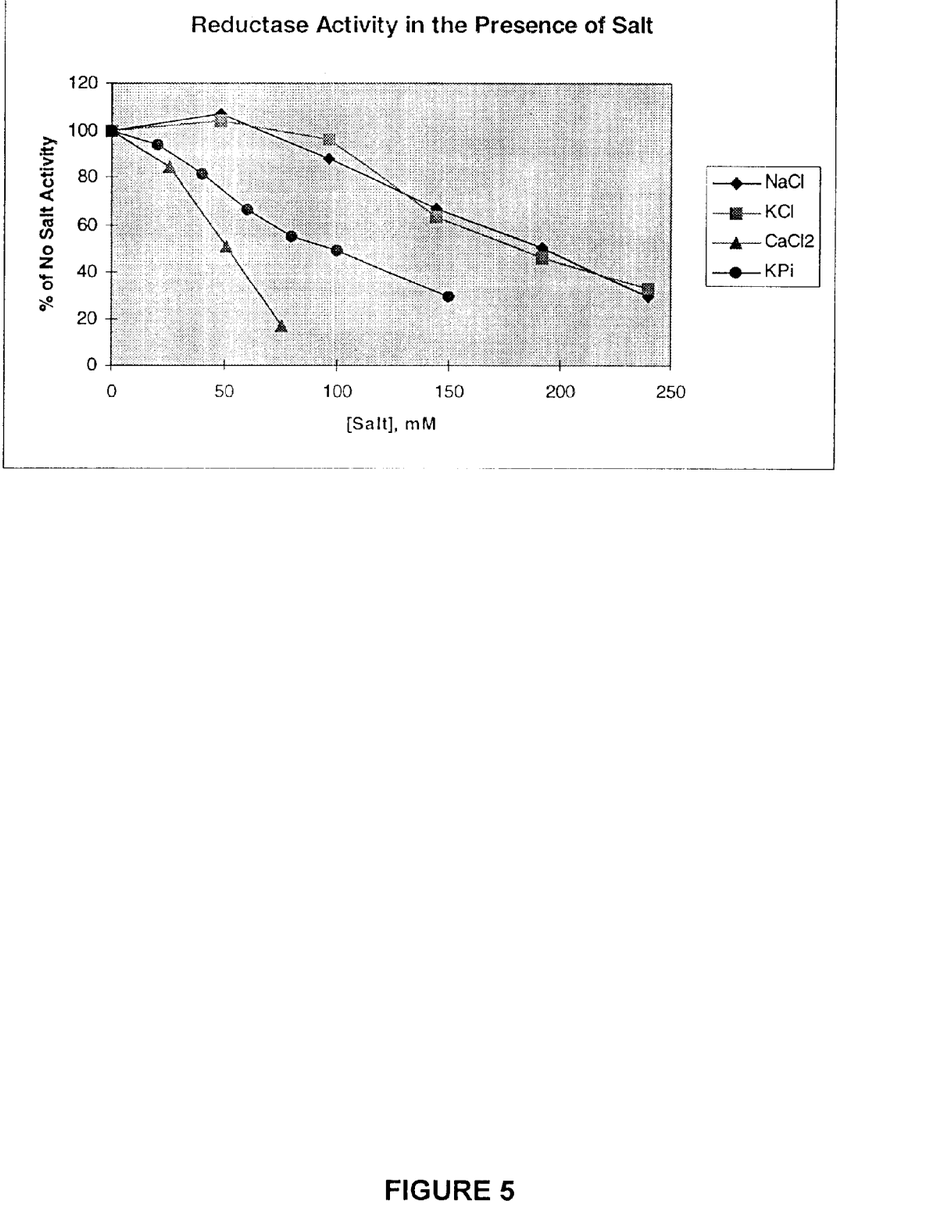
FIG. 5 illustrates reductase activity at pH 7 in the presence of NaCl, KCl, CaCl or potassium phosphate (KPi). Initial rates were measured over 1 min.

As shown in FIG. 5, reductase activity stays the same or slightly increases when incubated with up to 100 mM NaCl or KCl. Activity then drops as salt concentrations are increased to 250 mM. Reductase activity drops in concentrations of CaCl2 or potassium phosphate of 20 mM or more. Reductase activity is therefore sensitive to ionic strength and not to a specific ion.

The reductase binding constant (Km) for NADPH in the presence of 200 mM NaCl was determined using standard biochemical techniques (Fersht, A. "Enzyme Structure and Mechanism" (1977) W. H. Freeman and Company). The reactions were done in pH 7 bis-tris buffer containing approximately 1.5 mg/ml DKG at 30° C. and varying amounts of NADPH. The Km for NADPH in the presence of 200 mM NaCl was found to increase 10–30 fold over the Km determined without NaCl. The maximal rate (Vmax) in salt was similar or slightly increased over the no-salt Vmax. One way to reduce the effect of salt on reductase activity is to increase the concentration of NADPH until it is at or above the Km under those conditions. Alternatively, charged species including KLG could be removed.

We claim:

1. A process for the non-fermentative production of 2-keto-D-gluconate (KDG) comprising,
   a) obtaining Pantoea cells which comprise a mutation of a naturally occurring membrane bound glucose dehydrogenase (GDH) Pantoea gene, said gene capable of being amplified by a Polymerase Chain Reaction (PCR) using primers of SEQ ID NO:1 and SEQ ID NO:2 said mutation resulting in the inactivation or elimination of the naturally occurring GDH gene product of said gene,
   b) providing a bioreactor with (i) said Pantoea cells, (ii) glucose, and (iii) GDH, wherein the GDH is from a source other than the naturally occurring membrane bound GDH of the Pantoea cells, and
   c) allowing in the bioreactor enzymatic oxidation of the glucose to yield gluconate and enzymatic oxidation of the gluconate to yield KDG.

2. A process for the non-fermentative production of 2-keto-D-gluconate (KDG) from *Pantoea citrea* cells comprising,
   a) obtaining *Pantoea citrea* cells which comprise (i) a mutation of a naturally occurring membrane bound glucose dehydrogenase (GDH) *Pantoea citrea* gene said gene capable of being amplified by a Polymerase Chain Reaction (PCR) using primers of SEQ ID NO:1 and SEQ ID NO:2 and wherein said mutation results in the inactivation or elimination of the naturally occurring GDH gene product of said gene and (ii) a nucleic acid encoding a heterologous GDH,
   b) providing a bioreactor with said *Pantoea citrea* cells and glucose, and
   c) allowing in the bioreactor enzymatic oxidation of the glucose to yield gluconate and enzymatic oxidation of the gluconate to yield KDG.

3. The process according to claim 1, wherein the source of GDH is GDH obtained from the Pantoea cells, wherein said cells have been transformed with a polynucleotide encoding a heterologous GDH.

4. The process of claim 1, wherein said Pantoea cells are non-viable.

5. The process of claim 1, wherein said Pantoea cells are viable.

6. The process of claim 1 that is continuous.

7. The process of claim 1 that is batch.

8. The process of claim 1, wherein the bioreactor further comprises organic solvents.

9. The process of claim 1 further comprising recovering KDG from the bioreactor.

10. The process of claim 1 further comprising converting KDG to erythorbate.

11. The process of claim 1, wherein the Pantoea cells are lyophilized or permeabilized.

12. The process of claim 1 further comprising oxidizing the KDG to 2,5-diketo-D-gluconate (DKG) in the bioreactor.

13. The process of claim 1 further comprising recovering the DKG from the bioreactor.

14. The process of claim 2, wherein said *Pantoea citrea* cells are non-viable.

15. The process of claim 2, wherein said *Pantoea citrea* cells are viable.

16. The process of claim 2 that is continuous.

17. The process of claim 2 that is batch.

18. The process of claim 2, wherein the bioreactor further comprises organic solvents.

19. The process of claim 2 further comprising recovering KDG from the bioreactor.

20. The process of claim 2 further comprising converting KDG to erythorbate.

21. The process of claim 2, wherein the *Pantoea citrea* are lyophilized or permeabilized.

22. The process of claim 2 further comprising oxidizing the KDG to 2,5-diketo-D-gluconate (DKG) in the bioreactor.

23. The process of claim 2 further comprising recovering the DKG from the bioreactor.

24. The process of claim 3, wherein the heterologous GDH is a cytosolic NADP+ dependent GDH.

* * * * *

SEQUENCE LISTING

<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Synthetic

```
-continued

<400> SEQUENCE: 1
agggagtgct tactacctta tctgcggtat a                              31

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
cgctagctgt gcaatccatt gattttgcac a                              31
```